(12) United States Patent
Lindner et al.

(10) Patent No.: US 11,089,970 B2
(45) Date of Patent: Aug. 17, 2021

(54) IMAGING FLUID FLOW INTO A REGION OF INTEREST

(71) Applicant: KONINKLIJKE PHILIPS N.V., Eindhoven (NL)

(72) Inventors: Thomas Lindner, Eindhoven (NL); Michael Helle, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 1180 days.

(21) Appl. No.: 15/172,204

(22) Filed: Jun. 3, 2016

(65) Prior Publication Data

US 2016/0360979 A1 Dec. 15, 2016

(30) Foreign Application Priority Data

Jun. 12, 2015 (EP) ..................................... 15171895

(51) Int. Cl.
| | |
|---|---|
| *A61B 5/026* | (2006.01) |
| *G01R 33/54* | (2006.01) |
| *G01R 33/563* | (2006.01) |
| *A61B 5/00* | (2006.01) |
| *G01R 33/483* | (2006.01) |

(52) U.S. Cl.
CPC .......... *A61B 5/0263* (2013.01); *A61B 5/0042* (2013.01); *A61B 5/0044* (2013.01); *G01R 33/54* (2013.01); *G01R 33/5635* (2013.01); *G01R 33/56308* (2013.01); *G01R 33/4838* (2013.01)

(58) Field of Classification Search
CPC ... A61B 5/0263; A61B 5/0042; A61B 5/0044; G01R 33/54; G01R 33/56308; G01R 33/5635; G01R 33/4838
See application file for complete search history.

(56) References Cited

U.S. PATENT DOCUMENTS

| | | | | |
|---|---|---|---|---|
| 4,812,760 | A | * | 3/1989 | Bottomley ........... G01R 33/446 324/309 |
| 5,842,989 | A | * | 12/1998 | Zur ........................ A61B 5/055 600/410 |
| 5,926,021 | A | | 7/1999 | Hennig |
| 8,332,010 | B2 | | 12/2012 | Edelman |

(Continued)

OTHER PUBLICATIONS

Zhao, Feng, Jon-Fredrik Nielsen, and Douglas C. Noll. "Four dimensional spectral-spatial fat saturation pulse design." Magnetic resonance in medicine 72, No. 6 (2014): 1637-1647.*

(Continued)

*Primary Examiner* — Carolyn A Pehlke

(57) ABSTRACT

A magnetic resonance imaging system (100) for acquiring magnetic resonance data (141) from an imaging zone (108) includes a memory (134, 136) for storing machine executable instructions (150, 152, 154, 156) and pulse sequence commands (140). The pulse sequence commands cause the magnetic resonance imaging system to provide at least one spatially selective saturation pulse (408, 410) to at least one selected volume (124, 124') that is at least partially outside of a region of interest (123) and within the imaging zone. The magnetic resonance imaging system performs a non-selective inversion (412) of spins in the region of interest followed by a readout (414) of the magnetic resonance data which is reconstructed (202) into an image (142).

19 Claims, 4 Drawing Sheets

(56) References Cited

U.S. PATENT DOCUMENTS

| | | | | | |
|---|---|---|---|---|---|
| 9,035,652 | B2* | 5/2015 | Nishihara | ............... | A61B 5/055 324/309 |
| 2011/0071382 | A1* | 3/2011 | Miyazaki | ........... | G01R 33/5635 600/413 |
| 2012/0271158 | A1 | 10/2012 | Peteo | | |
| 2014/0378826 | A1 | 12/2014 | Edelman | | |
| 2015/0272453 | A1* | 10/2015 | Heberlein | .......... | G01R 33/5676 600/419 |
| 2015/0309134 | A1* | 10/2015 | Meakin | ................ | A61B 5/0263 324/309 |
| 2016/0143545 | A1* | 5/2016 | Nishihara | ............... | A61B 5/055 600/411 |
| 2016/0338600 | A1* | 11/2016 | Edelman | ............... | A61B 5/7207 |

OTHER PUBLICATIONS

Definition of readout gradient (https://www.mr-tip.com/serv1.php?type=db1&dbs=Readout%20Gradient, retrieved on Jun. 8, 2019).*
Nishihara, Takashi, Hiroyuki Itagaki, Chikako Moriwake, David A. Lampman, Tetsuhiko Takahashi, Yosuke Hirata, Kohsuke Kudo, and Makoto Sasaki. "Selective TOF MRA using Beam Saturation pulse."*
Nakamura, Masanobu, et al. "Vessel-selective, non-contrast enhanced, time-resolved MR angiography with vessel-selective arterial spin labeling technique (CINEMA-SELECT) in intracranial arteries." Radiological physics and technology 6, No. 2 (2013): 327-334.*
Lindner T Jensen-Kondering U, Wodarg F, Jansen O, Helle M. Non-Contrast Enhanced 4D Artery-Selective MR Angiography Using Spatially Selective Saturation. Proc Intl Soc Magn Reson Med. 2015.*
Hartkamp, Nolan S., Esben T. Petersen, Jill B. De Vis, Reinoud PH Bokkers, and Jeroen Hendrikse. "Mapping of cerebral perfusion territories using territorial arterial spin labeling: techniques and clinical application." NMR in Biomedicine 26, No. 8 (2013): 901-912.*
Helle, Michael, Susanne Rüfer, Matthias JP van Osch, Olav Jansen, and David G. Norris. "Selective multivessel labeling approach for perfusion territory imaging in pseudo-continuous arterial spin labeling." Magnetic resonance in medicine 68, No. 1 (2012): 214-219.*
Hartung et al, "Magnetic resonance angiography: current status and future directions" J Cardiovasc Magn Reson. Mar. 9, 2011;13:19.
Ito, et al. "Noninvasive Evaluation of Collateral Blood Flow through Circle of Willis in Cervical Carotid Stenosis Using Selective Magnetic Resonance Angiography;" J Stroke Cerebrovasc Dis. May-Jun. 2014;23(5):1019-23.
Maleki M., Dai W, Alsop DC. "Optimization of background suppression for arterial spin labeling perfusion imaging" MAGMA. Apr. 2012;25(2):p. 127-33.
Johst et al, "Time-of-flight magnetic resonance angiography at 7 T using venous saturation pulses with reduced flip angles" Investigative Radiology, 2012 47(8) p. 445-450.
Bottomley et al "Two Dimensional Spatially Selective Spin Inversion and Spin-Echo Refocusing with a Single Nuclear Magnetic Resonance Pulse" Journal of Applied Physics, 1987 62910) p. 4284-4290.

* cited by examiner

IMAGING FLUID FLOW INTO A REGION OF INTEREST

CROSS-REFERENCE TO PRIOR APPLICATIONS

This application claims the benefit or priority of EP application No. 15171895.4 filed on Jun. 12, 2014 which is incorporated herein in whole by reference.

TECHNICAL FIELD OF THE INVENTION

The invention relates to magnetic resonance imaging, in particular to the imaging or mapping of fluid flow into a region of interest.

BACKGROUND OF THE INVENTION

A large static magnetic field is used by Magnetic Resonance Imaging (MRI) scanners to align the nuclear spins of atoms as part of the procedure for producing images within the body of a patient. This large static magnetic field is referred to as the BO field.

During an MRI scan, Radio Frequency (RF) pulses generated by one or more transmitter coils cause perturbations to the local magnetic field, and RF signals emitted by the nuclear spins are detected by one or more receiver coils. These RF signals are used to construct the MR images. Magnetic resonance imaging may be used to perform various methods of magnetic resonance angiography. The journal article Hartung et. al. "Magnetic resonance angiography: current status and future directions," Journal of Cardiovascular Magnetic Resonance 2011, 13:19 provides a review of various magnetic resonance angiography techniques.

United States patent application US 2014/0378826 A1 discloses a system and method for producing an image of a vascular structure of a subject using a magnetic resonance imaging (MRI) system includes performing a first pulse sequence to acquire a flow-dependent imaging data set from the stack of prescribed imaging slices following a first quiescent inflow time period (QITP). The process also includes performing a second pulse sequence without suppressing signal from spins flowing into the stack of prescribed imaging slices through either of the veins or arteries to acquire a flow-independent imaging data set. The flow-dependent imaging data and the flow-independent imaging data are subtracted to create a difference image of the stack of prescribed imaging slices illustrating the at least one of the arteries and the veins as having a bright contrast and another of the arteries and veins as having a suppressed contrast.

The journal article Ito K, et al. Noninvasive Evaluation of Collateral Blood Flow through Circle of Willis in Cervical Carotid Stenosis Using Selective Magnetic Resonance Angiography; J Stroke Cerebrovasc Dis. 2014 May-June;23(5):1019-23. doi: 10.1016/j.jstrokecerebrovasdis.2013.08.018. (hereafter "Ito et. al.") discloses the use of cylindrical presaturation pulses for selective magnetic resonance angiography.

SUMMARY OF THE INVENTION

The invention provides for a magnetic resonance imaging system, a method, and a computer program product in the independent claims. Embodiments are given in the dependent claims.

As will be appreciated by one skilled in the art, aspects of the present invention may be embodied as an apparatus, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer executable code embodied thereon.

Any combination of one or more computer readable medium(s) may be utilized. The computer readable medium may be a computer readable signal medium or a computer readable storage medium. A 'computer-readable storage medium' as used herein encompasses any tangible storage medium which may store instructions which are executable by a processor of a computing device. The computer-readable storage medium may be referred to as a computer-readable non-transitory storage medium. The computer-readable storage medium may also be referred to as a tangible computer readable medium. In some embodiments, a computer-readable storage medium may also be able to store data which is able to be accessed by the processor of the computing device. Examples of computer-readable storage media include, but are not limited to: a floppy disk, a magnetic hard disk drive, a solid state hard disk, flash memory, a USB thumb drive, Random Access Memory (RAM), Read Only Memory (ROM), an optical disk, a magneto-optical disk, and the register file of the processor. Examples of optical disks include Compact Disks (CD) and Digital Versatile Disks (DVD), for example CD-ROM, CD-RW, CD-R, DVD-ROM, DVD-RW, or DVD-R disks. The term computer readable-storage medium also refers to various types of recording media capable of being accessed by the computer device via a network or communication link. For example a data may be retrieved over a modem, over the internet, or over a local area network. Computer executable code embodied on a computer readable medium may be transmitted using any appropriate medium, including but not limited to wireless, wire line, optical fiber cable, RF, etc., or any suitable combination of the foregoing.

A computer readable signal medium may include a propagated data signal with computer executable code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

'Computer memory' or 'memory' is an example of a computer-readable storage medium. Computer memory is any memory which is directly accessible to a processor. 'Computer storage' or 'storage' is a further example of a computer-readable storage medium. Computer storage is any non-volatile computer-readable storage medium. In some embodiments computer storage may also be computer memory or vice versa.

A 'processor' as used herein encompasses an electronic component which is able to execute a program or machine executable instruction or computer executable code. References to the computing device comprising "a processor" should be interpreted as possibly containing more than one processor or processing core. The processor may for instance be a multi-core processor. A processor may also refer to a collection of processors within a single computer system or distributed amongst multiple computer systems. The term computing device should also be interpreted to possibly refer to a collection or network of computing devices each comprising a processor or processors. The computer executable code may be executed by multiple processors that may be within the same computing device or which may even be distributed across multiple computing devices.

Computer executable code may comprise machine executable instructions or a program which causes a processor to perform an aspect of the present invention. Computer executable code for carrying out operations for aspects of the present invention may be written in any combination of one or more programming languages, including an object oriented programming language such as Java, Smalltalk, C++ or the like and conventional procedural programming languages, such as the C programming language or similar programming languages and compiled into machine executable instructions. In some instances the computer executable code may be in the form of a high level language or in a pre-compiled form and be used in conjunction with an interpreter which generates the machine executable instructions on the fly.

The computer executable code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described with reference to flowchart illustrations and/or block diagrams of methods, apparatus (systems) and computer program products according to embodiments of the invention. It is understood that each block or a portion of the blocks of the flowchart, illustrations, and/or block diagrams, can be implemented by computer program instructions in form of computer executable code when applicable. It is further understood that, when not mutually exclusive, combinations of blocks in different flowcharts, illustrations, and/or block diagrams may be combined. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

A 'user interface' as used herein is an interface which allows a user or operator to interact with a computer or computer system. A 'user interface' may also be referred to as a 'human interface device.' A user interface may provide information or data to the operator and/or receive information or data from the operator. A user interface may enable input from an operator to be received by the computer and may provide output to the user from the computer. In other words, the user interface may allow an operator to control or manipulate a computer and the interface may allow the computer indicate the effects of the operator's control or manipulation. The display of data or information on a display or a graphical user interface is an example of providing information to an operator. The receiving of data through a keyboard, mouse, trackball, touchpad, pointing stick, graphics tablet, joystick, gamepad, webcam, headset, pedals, wired glove, remote control, and accelerometer are all examples of user interface components which enable the receiving of information or data from an operator.

A 'hardware interface' as used herein encompasses an interface which enables the processor of a computer system to interact with and/or control an external computing device and/or apparatus. A hardware interface may allow a processor to send control signals or instructions to an external computing device and/or apparatus. A hardware interface may also enable a processor to exchange data with an external computing device and/or apparatus. Examples of a hardware interface include, but are not limited to: a universal serial bus, IEEE 1394 port, parallel port, IEEE 1284 port, serial port, RS-232 port, IEEE-488 port, bluetooth connection, wireless local area network connection, TCP/IP connection, ethernet connection, control voltage interface, MIDI interface, analog input interface, and digital input interface.

A 'display' or 'display device' as used herein encompasses an output device or a user interface adapted for displaying images or data. A display may output visual, audio, and or tactile data. Examples of a display include, but are not limited to: a computer monitor, a television screen, a touch screen, tactile electronic display, Braille screen, Cathode ray tube (CRT), Storage tube, Bi-stable display, Electronic paper, Vector display, Flat panel display, Vacuum fluorescent display (VF), Light-emitting diode (LED) displays, Electroluminescent display (ELD), Plasma display panels (PDP), Liquid crystal display (LCD), Organic light-emitting diode displays (OLED), a projector, and Head-mounted display.

Magnetic Resonance (MR) data is defined herein as being the recorded measurements of radio frequency signals emitted by atomic spins using the antenna of a magnetic resonance apparatus during a magnetic resonance imaging scan. Magnetic resonance data is an example of medical image data. A Magnetic Resonance (MR) image is defined herein as being the reconstructed two or three dimensional visualization of anatomic data contained within the magnetic resonance data. This visualization can be performed using a computer.

In one aspect the invention provides for a magnetic resonance imaging system for acquiring magnetic resonance data from an imaging zone. The imaging zone is a region where a magnetic field of sufficient strength and uniformity has been generated which enables magnetic resonance imaging to be performed within the imaging zone.

The magnetic resonance imaging system comprises a memory for storing machine-executable instructions and pulse sequence commands. The pulse sequence commands cause the magnetic resonance imaging system to provide at least one spatially selective saturation pulse to at least one selected volume. Wherein the at least one selected volume is at least partially outside of a region of interest and the at least one selected volume is within the imaging zone. The region of interest is within the imaging zone. The pulse sequence commands further cause the magnetic resonance imaging system to perform a non-selective inversion of spins in the region of interest. The pulse sequence commands further cause the magnetic resonance imaging system to perform a readout of the magnetic resonance data for the region of interest. During the step of the readout the magnetic resonance data is acquired. The at least one spatially selective saturation pulses are temporally performed before the readout of the magnetic resonance data.

The magnetic resonance imaging system further comprises a processor for controlling the magnetic resonance imaging system. Execution of the machine-executable instructions causes the processor to acquire the magnetic resonance data by controlling the magnetic resonance imaging system with the pulse sequence commands. Execution of the machine-executable instructions further causes the processor to reconstruct an image from the magnetic resonance data. This example may be beneficial because it may be possible to image the flow of fluid into the region of interest. The at least one spatially selective saturation pulse may be used to control the source of the fluid that is imaged.

In another embodiment the pulse sequence commands cause the magnetic resonance imaging system to perform a non-selective pre-saturation of the region of interest. At least one of the at least one spatially selective saturation pulses are temporally performed between the non-selective pre-saturation of the region of interest and the non-selected inversion of the region of interest.

In another embodiment the image is a fluid flow map of fluid flow into the region of interest from a region outside of the region of interest and from outside of the at least one selected volume.

In another embodiment the at least one spatially selective saturation pulse comprises at least one distinct spatially selective saturation pulse for each of the multiple selected volumes.

In another embodiment a portion of the at least one spatially selective saturation pulse is temporally performed between the non-selected inversion of spins in the region of interest and the readout of the magnetic resonance data.

In another embodiment at least two of the multiple spatially selective pulses suppress a chosen volume. The chosen volume is one of the at least one selected volumes.

A particular spatially selective pulse may be repeated multiple times within a particular pulse sequence repetition. In some examples it could be that you suppress volumes before and after the inversion. One could also suppress the same volume multiple times before and after the inversion. This may be particularly beneficial when there is a particularly large fluid flow into the region of interest.

In another embodiment the spatially selective RF excitation is a multi-dimensional radio-frequency pulse. The journal article Bottomely et al, J. Appl. Phys. 62 (10), 1987 pp. 4284-4290 describes a number of different spatially selective RF excitations.

In another embodiment the spatially selective radio frequency excitation is a cylindrical saturation pulse.

In another embodiment the spatially selective RF excitation is a sombrero pulse.

In another embodiment the spatially selective RF excitation is a doughnut pulse or doughnut shape pulse.

In another embodiment the spatially selective RF excitation is a stalagmite pulse.

In another embodiment the spatially selective RF excitation is a two-dimensional pulse.

In another embodiment the spatially selective RF excitation is an egg carton pulse.

In another embodiment the pulse sequence commands cause the magnetic resonance imaging system to perform lipid suppression of the region of interest before performing the readout of the magnetic resonance data for the region of interest. Lipid suppression may for example be a fat suppressing pulse sequence.

In another embodiment the lipid suppression is performed according to a spectral pre-saturation within inversion recovery protocol.

In another embodiment the lipid suppression is a SPIR imaging protocol.

In another embodiment the lipid suppression is a SPAIR imaging protocol.

In another embodiment the lipid suppression is a ProSet imaging protocol.

In another embodiment the lipid suppression is according to a Dixon imaging protocol. For example in a Dixon method a fat and a water image are acquired. A review of common Dixon techniques may for instance be found in the Handbook of MRI Pulse Sequences by Bernstein et al. (see pages 857-887).

In another embodiment the acquiring of the magnetic resonance data by controlling the magnetic resonance imaging system with the pulse sequence commands and the reconstructing of the image from the magnetic resonance data are performed repeatedly. Execution of the machine-executable instructions causes the processor to repeatedly append the image to a time-dependent image. This embodiment may be beneficial because a time sequence of the flow of fluid into a region of interest can be imaged repeatedly.

In another embodiment execution of the machine-executable instructions cause the processor to receive volume placement data. The volume placement data is descriptive of the location for each of the at least one selected volume. Execution of the machine-executable instructions cause the processor to adjust the pulse sequence data so that each of the at least one volume is specified by the volume placement data.

In some examples the volume placement data could be received manually from the user interface. In other examples the volume placement data may be pre-stored or may be received over a network or other connection.

In another embodiment the volume placement data may be received by an algorithm that automatically generates data for placing the selected volumes outside of the region of interest. For example an image segmentation may be performed and the volume placement data may be derived from this image segmentation.

In another embodiment execution of the processor to receive anatomical data descriptive of the subject. The anatomical data is further descriptive of one or more veins or arteries connected with an anatomical volume. The anatomical volume is within the region of interest. Execution of the machine-executable instructions further causes the processor to generate the volume placement data from the anatomical volume.

In another embodiment the volume placement data is generated from the anatomical volume by any one of the following: by executing an image segmentation algorithm and by receiving the volume placement data in response to displaying the anatomical data on the user interface.

In another embodiment execution of the machine-executable instructions further cause the processor to acquire scouting magnetic resonance data by controlling the magnetic resonance imaging system with the imaging pulse sequence commands. The imaging pulse sequence commands specify an image volume. The region of interest is within the image volume. Execution of the machine-executable instructions further cause the processor to reconstruct a scouting magnetic resonance image from the scouting magnetic resonance data. The scouting magnetic resonance image is the anatomical data.

In another aspect the invention provides for a method of operating a magnetic resonance imaging system for acquiring magnetic resonance data from an imaging zone. The method comprises the step of acquiring the magnetic resonance data by controlling the magnetic resonance imaging system with pulse sequence commands.

The pulse sequence commands cause the magnetic resonance imaging system to provide at least one spatially selective saturation pulse to at least one selected volume. The at least one selected volume is at least partially outside of the region of interest. The at least one selected volume is within the imaging zone. The region of interest is within the imaging zone. The pulse sequence commands further cause the magnetic resonance imaging system to perform a non-selective version of spins in the region of interest. The pulse sequence commands further cause the magnetic resonance imaging system to perform a readout of the magnetic resonance data for the region of interest. The method further comprises reconstructing an image from the magnetic resonance data.

In another embodiment the method is a method of mapping blood flow into the kidney.

In another embodiment the method is a method of mapping blood flow into the heart.

In another embodiment the method is a method of mapping blood flow from the coronary artery.

In another embodiment the method is a method of mapping blood flow from the pulmonary artery.

In another embodiment the method is a method of mapping blood flow into the ovary.

In another embodiment the method is a method of mapping blood flow from one or more ovary arteries.

In another embodiment the method is a method of mapping blood flow into an arm.

In another embodiment the method is a method of mapping blood flow into a finger.

In another embodiment the method is a method of mapping blood flow into a toe.

In another embodiment the method is a method of mapping blood flow into a foot.

In another embodiment the method is a method of mapping blood flow into a hand.

In another embodiment the method is a method of mapping blood flow into the liver.

In another embodiment the method is a method of mapping blood flow into the brain from one or more arteries.

In another embodiment the method is a method of mapping blood flow in arteries distal to a trifurcation in a tibia to selectively visualize the flow of blood from three individual arteries.

In another aspect the invention provides for a computer program product comprising machine-executable instructions for execution by a processor controlling the magnetic resonance imaging system for acquiring magnetic resonance data from an imaging zone. Execution of the machine-executable instructions causes the processor to acquire the magnetic resonance data by controlling the magnetic resonance imaging system with the pulse sequence commands. The pulse sequence commands cause the magnetic resonance imaging system to provide at least one spatially selective saturation pulse to at least one selected volume. The at least one selected volume is at least partially outside of a region of interest and within the imaging zone. The region of interest is within the imaging zone.

The pulse sequence commands further cause the magnetic resonance imaging system to perform a non-selective inversion of spins in the region of interest. The pulse sequence commands further cause the magnetic resonance imaging system to perform a readout of the magnetic resonance data for the region of interest. Execution of the machine-executable instructions further causes the processor to reconstruct an image from the magnetic resonance data.

It is understood that one or more of the aforementioned embodiments of the invention may be combined as long as the combined embodiments are not mutually exclusive.

BRIEF DESCRIPTION OF THE DRAWINGS

In the following preferred embodiments of the invention will be described, by way of example only, and with reference to the drawings in which.

DETAILED DESCRIPTION OF THE EMBODIMENTS

Like numbered elements in these figures are either equivalent elements or perform the same function. Elements which have been discussed previously will not necessarily be discussed in later figures if the function is equivalent.

Figure 1:
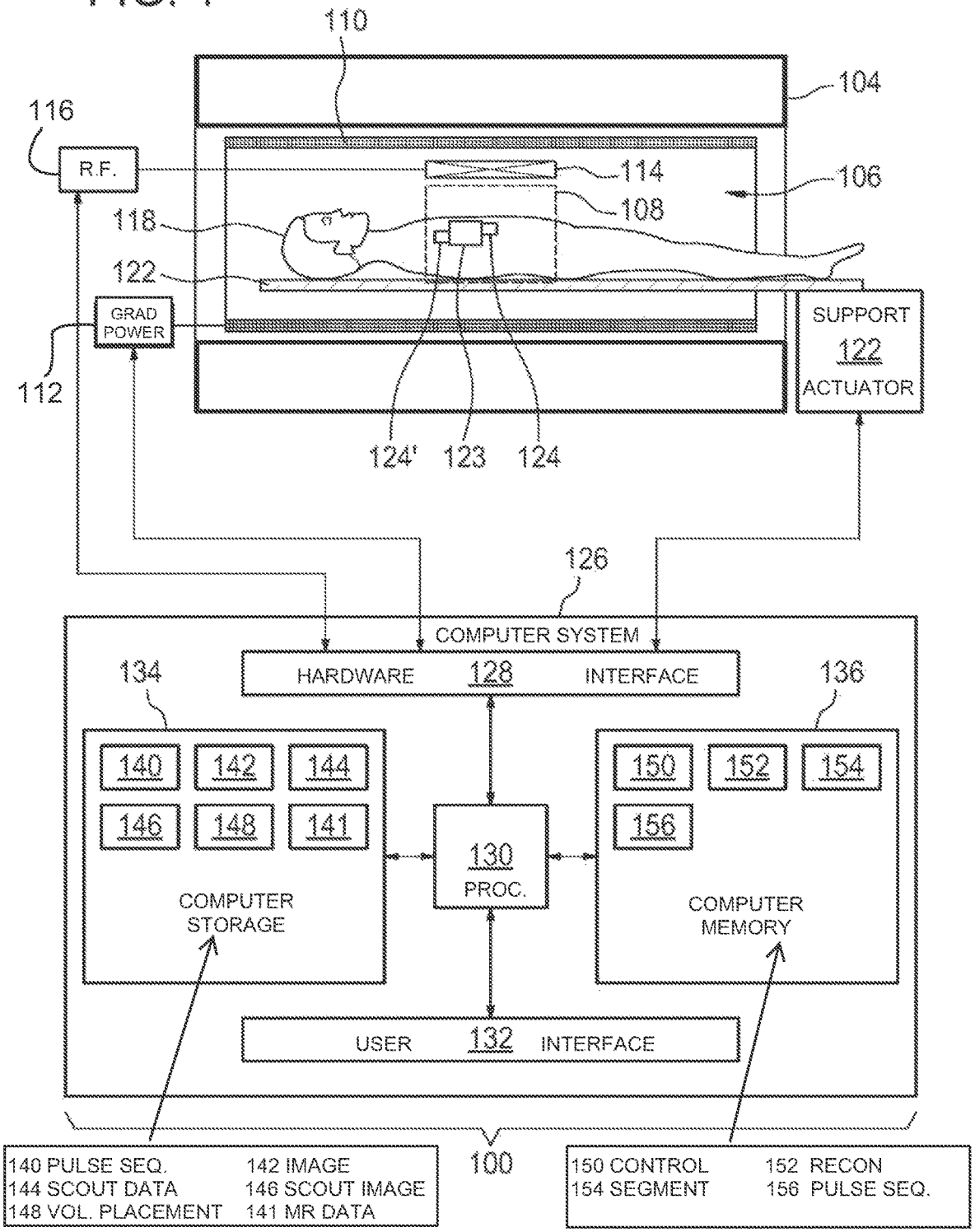
FIG. 1 illustrates an example of a magnetic resonance imaging system.

FIG. 1 shows an example of a magnetic resonance imaging system 100 with a magnet 104. The magnet 104 is a superconducting cylindrical type magnet 104 with a bore 106 through it. The use of different types of magnets is also possible; for instance it is also possible to use both a split cylindrical magnet and a so called open magnet. A split cylindrical magnet is similar to a standard cylindrical magnet, except that the cryostat has been split into two sections to allow access to the iso-plane of the magnet, such magnets may for instance be used in conjunction with charged particle beam therapy. An open magnet has two magnet sections, one above the other with a space in-between that is large enough to receive a subject: the arrangement of the two sections area similar to that of a Helmholtz coil. Open magnets are popular, because the subject is less confined. Inside the cryostat of the cylindrical magnet, there is a collection of superconducting coils. Within the bore 106 of the cylindrical magnet 104 there is an imaging zone 108 where the magnetic field is strong and uniform enough to perform magnetic resonance imaging.

Within the bore 106 of the magnet there is also a set of magnetic field gradient coils 110 which is used for acquisition of magnetic resonance data to spatially encode magnetic spins within the imaging zone 108 of the magnet 104. The magnetic field gradient coils 110 are connected to a magnetic field gradient coil power supply 112. The magnetic field gradient coils 110 are intended to be representative. Typically magnetic field gradient coils 110 contain three separate sets of coils for spatially encoding in three orthogonal spatial directions. A magnetic field gradient power supply supplies current to the magnetic field gradient coils. The current supplied to the magnetic field gradient coils 110 is controlled as a function of time and may be ramped or pulsed.

Adjacent to the imaging zone 108 is a radio-frequency coil 114 for manipulating the orientation of magnetic spins within the imaging zone 108 and for receiving radio transmissions from spins also within the imaging zone 108. The radio frequency antenna may contain multiple coil elements. The radio frequency antenna may also be referred to as a channel or antenna. The radio-frequency coil 114 is connected to a radio frequency transceiver 116. The radio-frequency coil 114 and radio frequency transceiver 116 may be replaced by separate transmit and receive coils and a separate transmitter and receiver. It is understood that the radio-frequency coil 114 and the radio frequency transceiver 116 are representative. The radio-frequency coil 114 is intended to also represent a dedicated transmit antenna and a dedicated receive antenna. Likewise the transceiver 116 may also represent a separate transmitter and receiver. The radio-frequency coil 114 may also have multiple receive/transmit elements and the radio frequency transceiver 116 may have multiple receive/transmit channels.

Within the bore 106 of the magnet 104 there is a subject support 120 which is attached to an optional actuator 122 that is able to move the subject support and the subject 118 through the imaging zone 108. Within the imaging zone 108 there is a region of interest 123. Adjacent to the region of interest 123 are two selected volumes 124, 124'.

The transceiver 116, the magnetic field gradient coil power supply 112 and the actuator 122 are all seen as being connected to a hardware interface 128 of computer system 126.

The computer storage 134 is shown as containing pulse sequence commands. The pulse sequence commands 140 cause the magnetic resonance imaging system 100 to provide at least one spatially selective saturation pulse to at least one selected volume 124, 124'. The at least one selected volume 124, 124' is at least partially outside of the region of interest 123 and within the imaging zone 108. The region of interest 123 is within the imaging zone 108. The pulse sequence commands 140 further cause the magnetic resonance imaging system 100 to perform a non-selective inversion of spins in the region of interest 123. The pulse sequence commands 140 further cause the magnetic resonance imaging system 100 to perform a readout of the magnetic resonance data 141 for the region of interest.

The computer storage 134 is further shown as containing magnetic resonance data 141 that was acquired by controlling the magnetic resonance imaging system 100 with the pulse sequence commands 140. The computer storage 134 is further shown as containing an image 142 that was reconstructed from the magnetic resonance data 141. The computer storage 134 is further shown as containing optional scouting magnetic resonance data. The scouting magnetic resonance data may for instance be acquired by controlling the magnetic resonance imaging system 100 with an additional set of pulse sequence commands. The computer storage 134 is further shown as containing a scouting magnetic resonance image that was reconstructed from the scouting magnetic resonance data 144. The scouting magnetic resonance image 146 is an optional feature. The computer storage 134 is further shown as containing volume placement data 148 that was generated from the scouting magnetic resonance image 146. The presence of the volume placement data 148 and the computer storage 134 is optional.

The computer memory 136 is shown as containing a control module 150. The control module 150 contains computer executable instructions that enable the processor 130 to control the operation and function of the magnetic resonance imaging system 100. For example the control module 150 may enable the processor 130 to use or execute the pulse sequence commands 140 to control the other portions of the magnetic resonance imaging system 100 to acquire the magnetic resonance data 141. The computer memory 136 is shown as containing an image reconstruction module 152 that enables the processor 130 to reconstruct the image 142 from the magnetic resonance data 141. It may also optionally enable the reconstruction of the scouting magnetic resonance image 146 from the scouting magnetic resonance data 144. The computer storage 136 is further shown as containing an image segmentation module 154. The image segmentation module may contain instructions which enable the processor 130 to generate the volume placement data 148 from the scouting magnetic resonance image 146. The image segmentation module 154 is an optional feature. The computer memory 136 is further shown as containing a pulse sequence modification module 156 which optionally enables the processor 130 to modify the pulse sequence commands 140 using the volume placement data 148.

The contents of the computer storage 134 and the computer memory 136 may be exchanged or the contents of one may be duplicated in the other.

Figure 2:
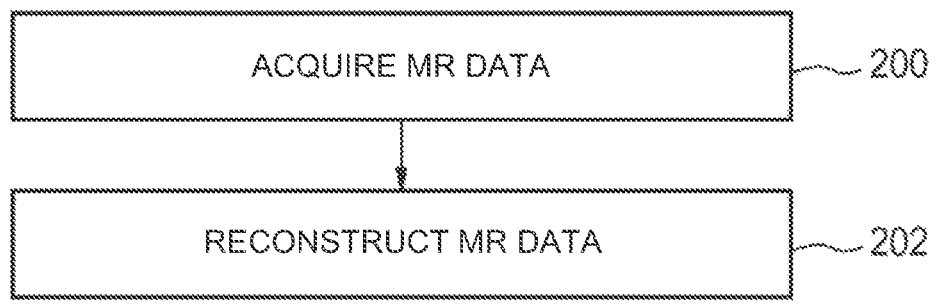
FIG. 2 shows a flow chart which shows a method of operating the magnetic resonance imaging system of FIG. 1.

FIG. 2 shows a flowchart which illustrates a method of operating the magnetic resonance imaging system 100 of FIG. 1. First in step 200 the magnetic resonance imaging system 100 is controlled using the pulse sequence commands 140 to acquire the magnetic resonance data 141. Next in step 202 the magnetic resonance image 142 is reconstructed from the magnetic resonance data 141.

Examples may provide for a method for artery-selective, time-resolved, non-contrast enhanced Magnetic Resonance Angiography based on the inflow effect of unsaturated arterial blood. Artery-selectivity is achieved via consecutively applied 2D RF-Pulses individually positioned over feeding arteries. Other arteries remain unsaturated and provide signal in the acquired images. Time-resolved imaging can be achieved by increasing the bolus length for each image acquisition. Background suppression is used to saturate static tissues in the image volume, thus, no subtraction is required.

Artery-selective imaging of the intracranial arteries is crucial in the differential diagnosis of cerebrovascular diseases. Non-contrast-enhanced magnetic resonance angiography (NCE-MRA) appears to be a valuable tool for the assessment of the intracranial arterial status, as there is neither X-Ray irradiation, nor contrast agent application involved, as compared to other imaging methods in radiology. However, in MRI, artery-selective imaging is a non-trivial problem to overcome, as traditionally this was only achievable using catheter angiography and selective injection of contrast agent. In recent years, a method of selective angiography using a single double-oblique cylindrical radiofrequency (RF) pulse was presented. This method may be applied in a time-of-flight (TOF) angiography sequence, resulting in static selective angiograms of brain supplying vessels, where one carotid artery was suppressed in the images. However, in some cases it is important to obtain information about only one vessel. Furthermore, also the hemodynamic information can be helpful to supply knowledge about blood flow properties in addition to morphological information.

Examples may provide for a means to visualize one or more brain supplying arteries on an individual basis in a complete non-invasive way by using MRI. Not only information about vessel morphology can be imaged, but also hemodynamic properties of the arterial blood flow can be obtained. Venous signal is suppressed for optimal evaluation of only the arterial architecture without decreasing image quality. No image subtraction is required, thus, making the presented method less sensitive to subject motion.

The gold standard method of obtaining selective angiograms is X-Ray digital subtraction angiography (DSA). This method relies on selectively placing an endovascular catheter through the iliac (or brachial) artery and injection of contrast agent. However, this method is invasive due to the need for placing an arterial access and the application of X-Rays and contrast agent. Furthermore, this method is time consuming due to elaborate preparations.

Currently available tomographic imaging methods do not allow for artery-selective imaging. This is especially true for contrast enhanced methods, such as computed tomography angiography (CTA) and contrast-enhanced MRA. In these methods, a bolus of contrast agent is injected intravenously. After passing through the pulmonary arteries and then being ejected from the heart, the bolus traverses into the arteries ("arterial phase") where image acquisition is subsequently performed as fast as possible to catch the first pass arterial inflow and visualize the hemodynamic properties. In fast CE-MRA methods, after the first pass of contrast agent into the brain, the later arriving arterial blood is visualized simultaneously with the venous outflow, which might degrade the image quality. While non-contrast enhanced methods pose an attractive alternative to contrast agent injection, they cannot be intrinsically performed artery-selective. The most commonly used method in Neuro-MRA is TOF Angiography, where the inflow of unsaturated arterial blood is used to form an image of the intracranial arteries.

The method presented in Ito et. al. is based on a standard TOF sequence, but with an additional oblique positioned cylindrical saturation pulse, allowing the suppression of a single artery. The standard TOF as well as the "Beam Sat" TOF provide excellent spatial resolution (<0.5 mm on 3T MRI machines) as well as high signal of the arteries. However, the methods lack hemodynamic information. Hemodynamic information can be obtained for instance by using phase-contrast angiography (PCA). Here, information about the flow is gathered by the application of a flow encoding gradient along the flow direction(s) of the arterial spins. Depending on the blood flow velocity, the individual spins express a phase shift, which can be used to draw conclusions on the direction and velocity of the blood flow. A limitation of this method is that the user has to choose a certain value for the velocity encoding prior to image acquisition, which might lead to false results when the chosen value is not adapted to the actual hemodynamic properties. A recently presented method for the acquisition of intracranial arteries is based on Arterial Spin Labeling (ASL). The basic principle of ASL Angiography is the inversion of the up streaming blood of a single artery or all arteries at once. After acquisition of an image with inversion (label) and an image without inversion (control), subsequent subtraction results in angiograms with high SNR, as the background signal is ideally cancelled out. However, image subtraction as a prerequisite and makes this method sensitive to subject motion and prolongs acquisition times.

This method allows acquiring time-resolved angiograms of a selected artery without the application of an external contrast agent. To achieve artery selectivity, individually placed cylindrical RF pulses are used. To achieve a good contrast between arteries and background (static tissue), background suppression is used. No image subtraction is needed which results in shorter overall scan time and makes the method less sensitive to subject motion.

The sequence consists of different blocks of preparatory RF pulses and gradients. Presaturation of the imaging volume is applied in order to saturate the longitudinal magnetization of static brain tissue (e.g. grey and white brain matter, cerebrospinal fluid). The inflow time can be chosen by the user and will determine the length of the generated blood bolus, thereby also the temporal resolution of the subsequently acquired images. After presaturation, cylindrical pulses are performed in a consecutive manner for the duration of the inflow time to selectively saturate the inflowing arterial blood of individual vessels.

The cylindrical saturation pulses are placed over selected arteries, leaving all other arteries unsaturated. For a predefined inflow time, the number of cylindrical saturation pulses is adapted accordingly, i.e. longer inflow times will require more cylindrical saturation pulses. In addition, the timing of one or more non-selective inversion pulses is adapted and applied in between the saturation pulses in order to ensure saturation of static tissue signal in the imaging volume at the time of data acquisition. The timing of the inversion pulses depends on the chosen inflow duration, as well as on the relaxation constants of the different tissues. Time-resolved imaging is achieved by increasing the inflow time for each acquired image, i.e. the number of cylindrical saturation pulses, thus the amount of saturated blood and the length of the blood bolus, respectively (see FIG. 4 below). At the time of image readout, the static brain tissue and the venous blood give nearly zero signal, as the longitudinal magnetization should be approximately zero at that time. Optimized saturation of different tissues in the imaging volume can be achieved by applying more than one inversion pulse.

Example for imaging of one selected carotid artery:
Presaturation of the imaging volume is achieved by using 90° WET pulses. Two differently positioned cylindrical RF pulses are applied consecutively to saturate the blood of other major brain feeding arteries, i.e. the vertebral arteries and contralateral carotid artery (FIG. 1). The cylindrical RF pulses of type jinc employ a diameter of 30 mm with 20 cycles in k-space, resulting in a total duration of 10 ms per pulse. The inversion pulse is applied at 450 ms after the presaturation module to saturate the static tissues in the image volume. Before image acquisition, a fat selective SPIR pulse is applied to selectively saturate the signal of the cranial bone marrow. Image acquisition consists of a standard RF spoiled (TFE) readout sequence. For the next time frame, the inflow time is increased by the time required for image data acquisition to ensure a consecutive acquisition of blood flow without temporal gaps. A sketch of the pulse sequence scheme is presented below in FIG. 4. The resulting time-resolved images for the right carotid artery are presented below in FIG. 5.

Figure 3:
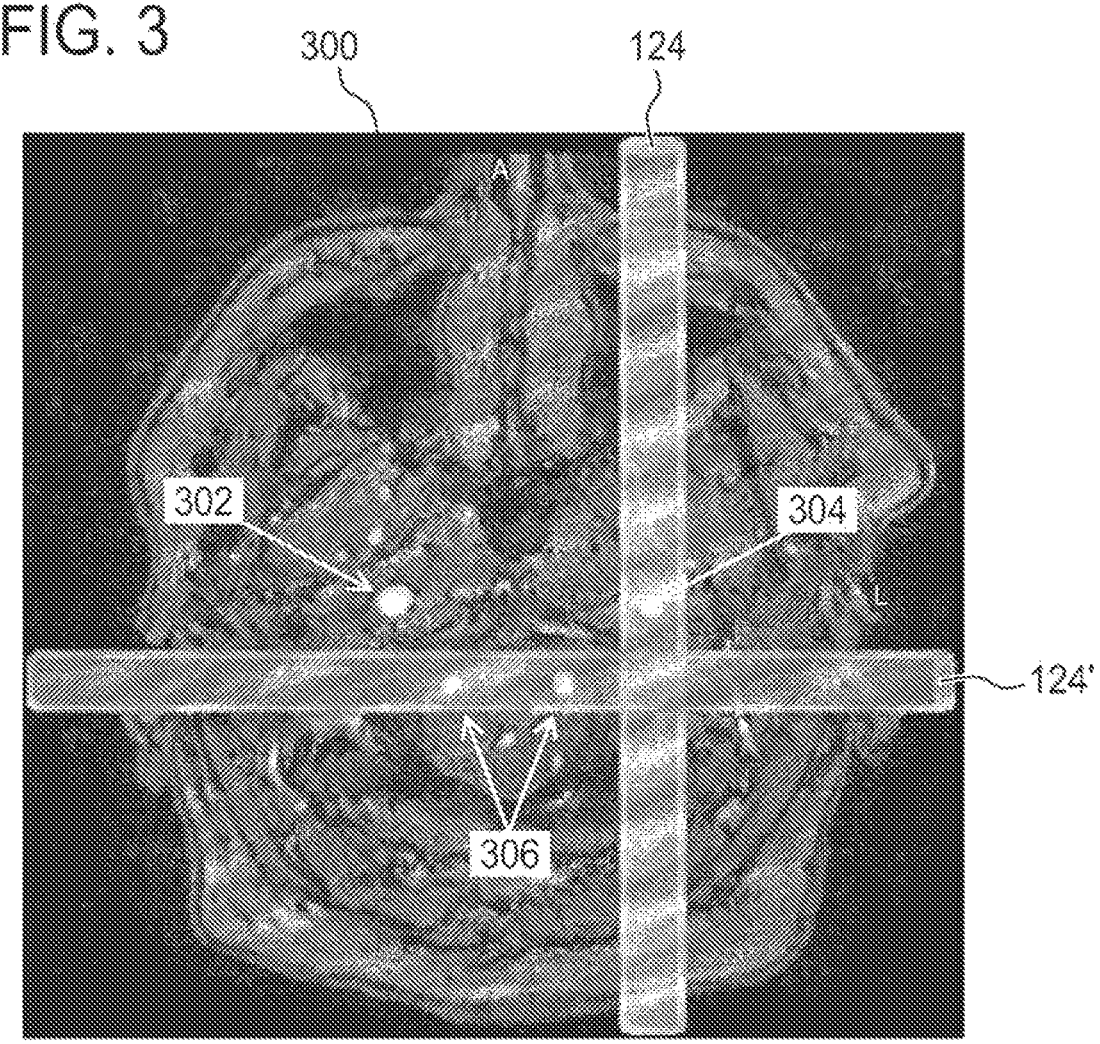
FIG. 3 shows a magnetic resonance image that shows the location of several different arteries and the placement of spatially selective saturation pulses.

FIG. 3 shows a magnetic resonance image 300 that shows the location of several different arteries 302, 304, 306. The right internal carotid artery is labeled 302. The left internal carotid artery is labeled 304. Also visible are several vertebral arteries 306. The box labeled 124' shows the location of a cylindrical saturation pulse that saturates blood passing through the vertebral arteries 306. The box labeled 124 shows the position of a further cylindrical saturation pulse that saturates blood passing through the left internal carotid artery 304. The view 300 shown in FIG. 3 is outside of the region of interest. This Fig. illustrates that only the blood passing through the right internal carotid artery 302 will enter the brain without being saturated. This enables the imaging of blood flow through the right internal carotid artery to be imaged.

Figure 4:
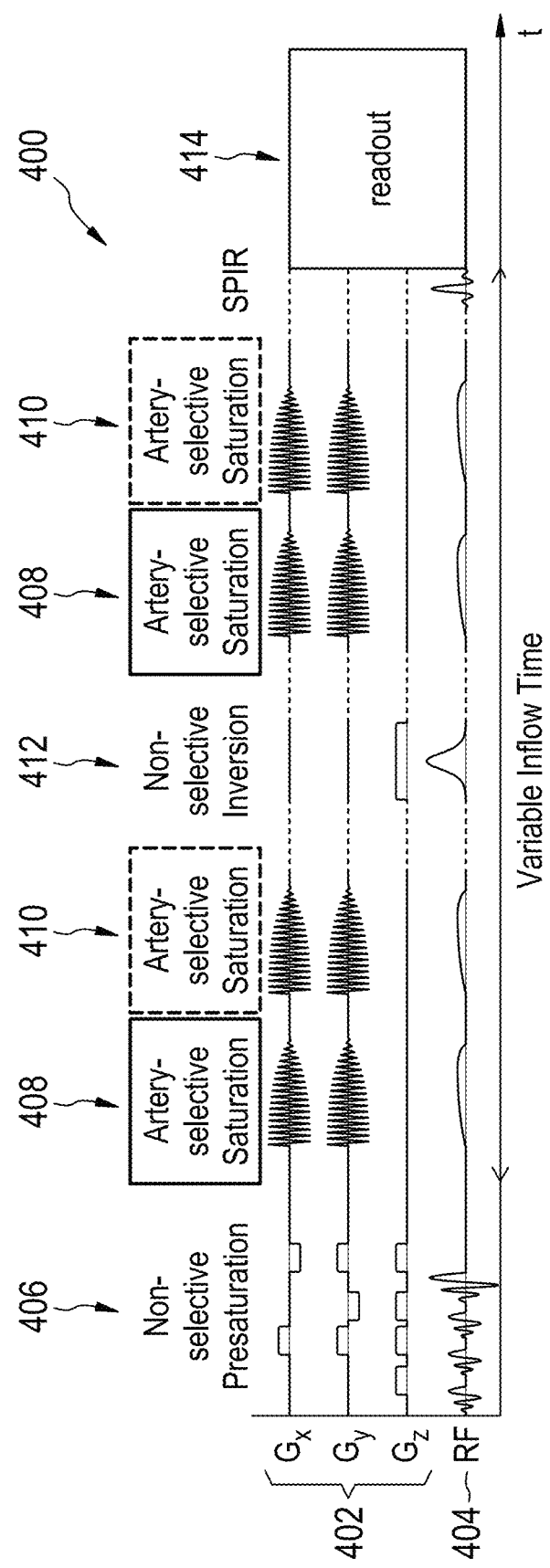
FIG. 4 shows a pulse sequence timing diagram 400 to be used for constructing the pulse sequence commands.

FIG. 4 shows a pulse sequence timing diagram 400 to be used for constructing the pulse sequence commands 140 of FIG. 1. The timing diagram is not complete and only several components are shown. The gradient pulses 402 are shown as is a RF transmit and/or receive channel 404. The pulse sequence 400 has several parts. There is a non-selective pre-saturation 406. The non-selective pre-saturation 406 in some instances may be optional. There are also several artery selected saturations 408 and 410 that are shown. For example the artery selected saturation 408 may be used for performing the saturation of region 124 in FIG. 3. The saturations 410 may be used for performing the saturation of the regions marked 124' in FIG. 3. During step 412 a non-selective inversion is performed in the region of interest 123. The two artery selected saturations 408 and 410 are performed again and then during a readout 414 of the magnetic resonance data the magnetic resonance data is acquired.

Figure 5:
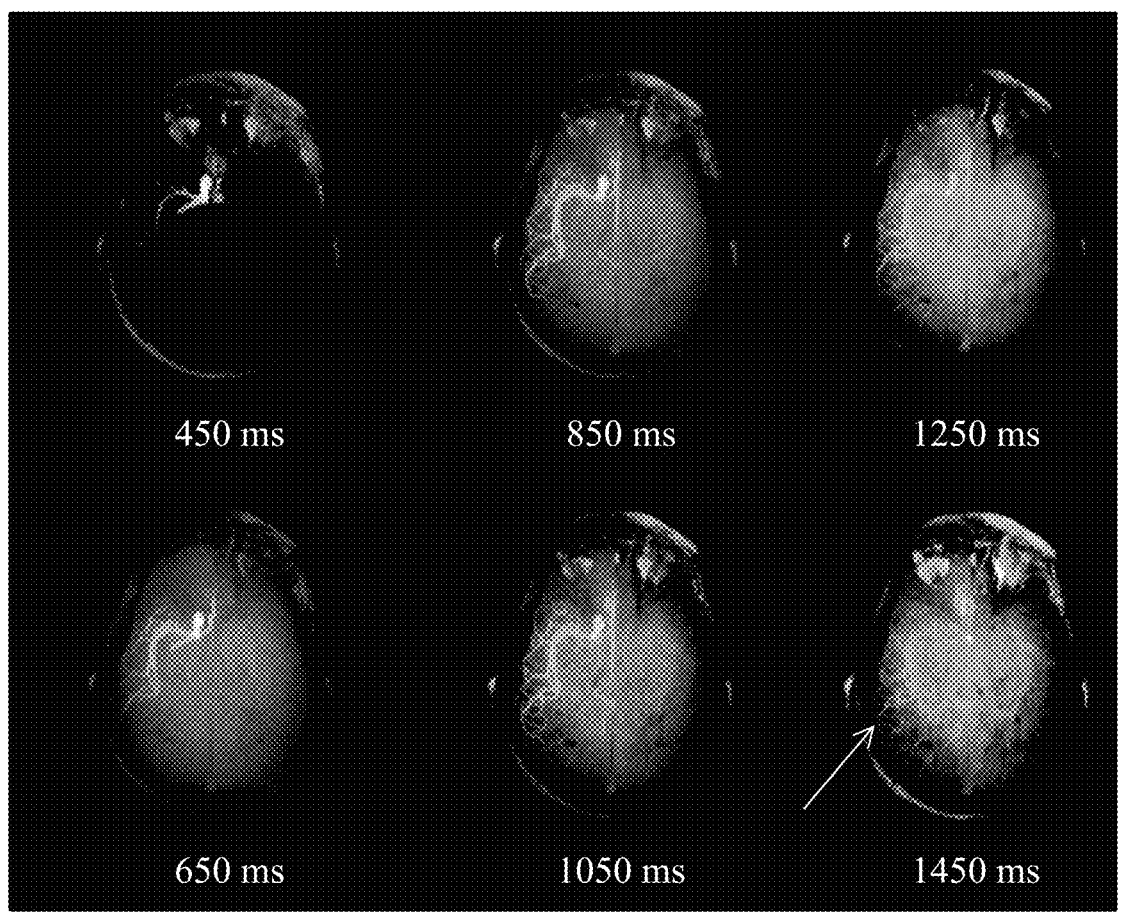
FIG. 5 shows a series of time resolved images which are the maximum intensity projections of the right internal carotid artery.

FIG. 5 shows a series of time resolved images which are the maximum intensity projections of the right internal carotid artery of a healthy volunteer with the corresponding in flow times of 450 ms, 650 ms, 850 ms, 1050 ms, 1250 ms, and 1450 ms. This for example may be performed using the pulse sequence of FIG. 4 with the placement of the volumes 124 and 124' as is shown in FIG. 3. The individual arteries are clearly delineated and provide a picture of the intercranial arterial status of two distal branches indicated by the arrow. No unwanted flow of the suppressed arteries 304, 306 is visible for different in flow times. In the later acquired images more noise from the background tissue is visible. Two or more inversion pulses with optimized timing may increase the saturation of different tissues.

The main applications of examples include visualization of the intracranial arterial architecture, e.g. to evaluate crossflow in patients with carotid or vertebro-basilar stenosis. In patients at risk for thromboembolic stroke or chronic stenosis, it could be possible to assess the potential of collateral flow inside the Circle of Willis to provide estimations on potential supply from other arteries. Furthermore, this method might help in the initial assessment of arteriovenous malformations or fistulas, providing the possibility of excluding several arteries as feeders.

The presented examples are not necessarily limited to the cerebral vasculature, but might also be used to visualize other arteries. These include selective visualization of the renal arteries, the coronary arteries, as well as the peripheral lower leg arteries.

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

LIST OF REFERENCE NUMERALS 100 magnetic resonance imaging system
104 magnet
106 bore of magnet
108 imaging zone
110 magnetic field gradient coils
112 magnetic field gradient coil power supply
114 radio-frequency coil
116 transceiver
118 subject
120 subject support
122 actuator
123 region of interest
124 selected volume
124' selected volume
126 computer system
128 hardware interface
130 processor
132 user interface
134 computer storage
136 computer memory
140 pulse sequence commands
141 magnetic resonance data
142 image (flow map)
144 scouting magnetic resonance data
146 scouting magnetic resonance image
148 volume placement data
150 control module
152 image reconstruction module
154 image segmentation module
156 pulse sequence modification module
200 acquire the magnetic resonance data by controlling the magnetic resonance imaging system with the pulse sequence command
202 reconstruct an image from the magnetic resonance data
300 magnetic resonance image
302 right internal carotid artery (RICA)
304 left internal carotid artery (LICA)
306 vertebral arteries (VA)

400 pulse sequence timing diagram
402 gradient pulses
404 RF transmit/receive
406 non-selective presaturation
408 selective saturation
410 selective saturation
412 non-selective saturation
414 readout of magnetic resonance data

The invention claimed is:

1. A magnetic resonance imaging system for acquiring magnetic resonance data from an imaging zone, the magnetic resonance imaging system comprising:
a memory including machine executable instructions and pulse sequence commands stored therein, wherein the pulse sequence commands cause a processor to control the magnetic resonance imaging system to:
perform a non-selective pre-saturation of a region of interest,
provide a first spatially selective saturation pulse for a first selected volume and a second spatially selective saturation pulse for a second selected volume, wherein the first and second spatially selective saturation pulses each include any one of: a multidimensional RF pulse, a cylindrical saturation pulse, a sombrero pulse, a donut pulse, a stalagmite pulse, a two dimensional pulse, and an egg carton pulse, and wherein the first and second selected volumes are at least partially outside of the region of interest, wherein the second selected volume is displaced from the first selected volume, wherein the first and second selected volumes are within the imaging zone, wherein the region of interest is within the imaging zone, and wherein the first and second spatially selective saturation pulses are provided sequentially,
perform a non-selective inversion of spins in the region of interest, wherein the sequential first and second selective saturation pulses are temporally provided between the non-selective pre-saturation of the region of interest and the non-selective inversion of the region of interest,
provide an additional spatially selective saturation pulses for each of the first and second selected volumes after the non-selective inversion of spins,
acquire the magnetic resonance data after the additional spatially selective saturation pulses, and
reconstruct a fluid flow map of fluid flow in the region of interest including fluids that flowed into the region of interest from the first and second selected volumes from the magnetic resonance data.

2. The magnetic resonance imaging system of claim 1, wherein the additional spatially selective pulses sequentially suppress the first and second selected volumes.

3. The magnetic resonance imaging system of claim 1, wherein the pulse sequence commands cause the magnetic resonance imaging system to perform lipid suppression of the region of interest before performing the readout of the magnetic resonance data for the region of interest.

4. The magnetic resonance imaging system of claim 3, wherein the lipid suppression includes any one of: a spectral pre-saturation with inversion recovery protocol, a SPIR imaging protocol, a SPAIR imaging protocol, a ProSet imaging protocol, and a Dixon imaging protocol.

5. The magnetic resonance imaging system of claim 1, wherein execution of the machine executable instructions causes the processor to:
receive volume placement data, wherein the volume placement data is descriptive of a location for each of the first and second selected volumes; and
adjust the pulse sequence data so that each of the first and second selected volumes is specified by the volume placement data.

6. The magnetic resonance imaging system of claim 1, wherein execution of the machine executable instructions further cause the processor to control the magnetic resonance system to:
acquire scouting magnetic resonance data by controlling the magnetic resonance imaging system with imaging pulse sequence commands, wherein the imaging pulse sequence commands specify an image volume, wherein the region of interest is within the image volume; and
reconstruct a scouting magnetic resonance image from the scouting magnetic resonance data.

7. The magnetic resonance imaging system of claim 6, wherein the scouting magnetic resonance image is descriptive of one or more veins or arteries connected with an anatomical volume within the region of interest.

8. A magnetic resonance imaging system for generating a fluid flow map of fluid flow in a region of interest within an imaging zone, the region of interest including a first blood vessel and a second blood vessel, the magnetic resonance imaging system including one or more processors configured to:
a) perform a non-selective pre-saturation of the region of interest;
b) applying at least a first spatially selective saturation pulse for a first selected volume, the first selected volume encompassing the first blood vessel at least partially outside of the region of interest and within an imaging zone;
c) after the at least one first spatially selective saturation pulse, applying at least a second spatially selective saturation pulse for a second selected volume, the second selected volume encompassing the second blood vessel at least partially outside of the region of interest and within an imaging zone;
d) after applying the second spatially selective saturation pulse, perform a non-selective inversion of spins in the region of interest;
e) after the non-selective inversion of spins, applying at least a third spatially selective saturation pulse for the first selected volume;
f) after the at least third spatially selective saturation pulse, applying at least a fourth spatially selective saturation pulse for the second selected region;
g) after the fourth spatially selective saturation pulse, perform a lipid suppression in the region of interest;
h) after the lipid suppression, read out magnetic resonance data from the imaging zone; and
i) reconstruct the fluid flow map of fluid flow in the region of interest from the magnetic resonance data without image subtraction.

9. The magnetic resonance imaging system of claim 8, wherein the first and second spatially selective saturation pulses are different from each other.

10. The magnetic resonance imaging system of claim 8, wherein the third and fourth spatially selective saturation pulses are different from each other.

11. The magnetic resonance imaging system of claim 8, wherein the first and third spatially selective saturation pulses overlay the first blood vessel and second and fourth spatially selective saturation pulses overlay the second blood vessel.

12. The magnetic resonance imaging system of claim 11, further including repeating steps a)-i), wherein the first second, third, and fourth spatially selective saturation pulses have different lengths in each repetition.

13. The magnetic resonance imaging system of claim 12, wherein the spatially selective saturation pulses are cylindrical pulses.

14. The magnetic resonance system of claim 11, wherein the lipid suppression includes one of a spectral pre-saturation inversion recovery protocol or a Dixon protocol.

15. A non-transitory computer-readable medium carrying software instructions to control the one or more processors of the magnetic resonance imaging system of claim 8 to perform steps a)-i).

16. The magnetic resonance system of claim 8, wherein the first and third spatially selective saturation pulses are distinct and wherein the second and fourth spatially selective saturation pulses are distinct.

17. A magnetic resonance imaging system for generating a fluid flow map of fluid flow in a region of interest including one or more processors configured to control the magnetic resonance imaging system to:
   a) perform a non-selective pre-saturation of the region of interest;
   b) after performing the non-selective pre-saturation of the region of interest, generate a first spatially selective saturation pulse in a first selected volume through which the fluid flows and a second spatially selective saturation pulse in a second selected volume, the first and second selected volumes being different from each other and being at least partially outside of the region of interest and wherein the second spatially selective saturation pulse is generated after the first spatially selective saturation pulse;
   c) after generating the second spatially selective pulse, perform a non-selected inversion spins in the region of interest;
   d) after the non-selective inversion of spins, generating a third spatially selective saturation pulse for the first selected volume;
   e) after generating the third spatially selective saturation pulse, generating a fourth spatially selective saturation pulse for the second selected volume;
   f) read out magnetic resonance data from the region of interest; and
   g) reconstruct the fluid flow map of the fluid flow for the region of interest from the read out magnetic resonance data without image subtraction.

18. The magnetic resonance imaging system of claim 17, wherein the first and second selected volumes are cylindrical and overlay spatially displaced first and second blood vessels, respectively.

19. A non-transitory computer-readable medium carrying software instructions to control the one or more processors of the magnetic resonance imaging system of claim 17 to perform steps a)-g).

* * * * *